Figure 1:
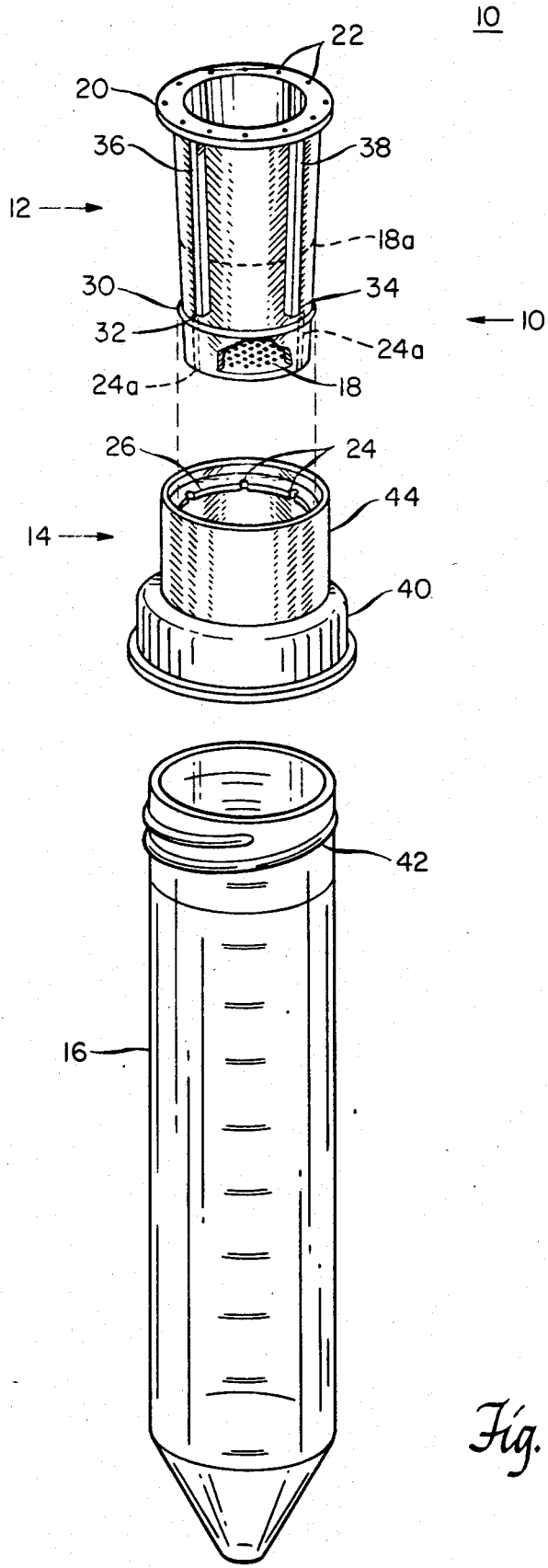

United States Patent [19]

Fay

[11] Patent Number: 4,675,110
[45] Date of Patent: Jun. 23, 1987

[54] FILTER DEVICE AND APPARATUS WITH MULTIPLE GAS RETURN PASSAGES

[75] Inventor: John E. Fay, Leominster, Mass.

[73] Assignee: Biomedical Polymers, Inc., Leominster, Mass.

[21] Appl. No.: 824,849

[22] Filed: Jan. 31, 1986

[51] Int. Cl.⁴ .............................................. B01D 23/20
[52] U.S. Cl. ..................................... 210/436; 210/446; 210/453; 210/455; 210/464; 210/472; 210/474; 210/477
[58] Field of Search ............... 210/436, 472, DIG. 24, 210/927, 464, 465, 473, 474, 445, 446, 450, 451, 453, 455, 456, 477, 479, 489; 55/159

[56] References Cited

U.S. PATENT DOCUMENTS 4,485,015 11/1984 Smith .................................. 210/472
4,525,276 6/1985 Toda et al. .......................... 210/472

Primary Examiner—Frank Sever
Attorney, Agent, or Firm—Joseph S. Iandiorio; Douglas E. Denninger

[57] ABSTRACT

A filter device and apparatus for filtering liquid from a collection vessel into a receptacle vessel, including a conduit, a filter in the conduit, and a rim spaced from the filter and forming an interference fit with the interior surface of the collection vessel. The rim has a plurality of openings spaced about its periphery. The device and apparatus further include means for removably securing the conduit to the receptacle vessel and a plurality of gas return passages, arranged about the exterior of the conduit, which connect the receptacle vessel to the openings in the rim.

22 Claims, 2 Drawing Figures

4,675,110

FILTER DEVICE AND APPARATUS WITH MULTIPLE GAS RETURN PASSAGES

FIELD OF INVENTION

This invention relates to a filter device with multiple pressure-equalization, gas-return passages and more particularly to such a filter device in which the passages are distributed peripherally about the filter.

BACKGROUND OF INVENTION

There are a number of applications in which solid particles are extracted from a liquid. Particles to be examined may be captured by a filter or may be passed by the filter while larger, undesired particles are blocked. Some applications involve separating parasite larvae and eggs from feces placed in a specimen vial to which a diluent liquid is added. One apparatus utilizes a funnel carrying a screen through which the feces-liquid mixture is poured from the specimen vial into a centrifuge tube. The screen catches large debris such as undigested vegetable matter and passes larvae, eggs and diluent liquid. The tube is centrifuged and the parasites are removed for examination.

In many fecal examination procedures, such as one using the above apparatus, the feces-liquid mixture is not maintained throughout the procedure in a closed system. In such cases the mixture is subject to spillage which invalidates the sample.

Another apparatus utilizes a double-ended cap which threadably engages both a specimen vial and a centrifuge tube. The cap carries a screen including a coaxial tube to provide for the passage of gas to equalize pressure between the tube and the vial. During use, feces and diluent liquid are added to the specimen vial and the cap with inverted centrifuge tube is screwed over its opening. The assembled apparatus is then inverted end-for-end to pass liquid and parasites into the centrifuge tube while blocking undesired debris.

The coaxial tube is required to prevent a vacuum from forming inside the specimen vial and to allow displacement of gas from the centrifuge tube. However, the single tube is easily blocked by debris. The apparatus often must be agitated frequently to clear the tube. Further, the tube may be crimped during manufacture or may become separated from the cap. When the tube is removed, little or no liquid passes through the screen.

Even when the coaxial tube operates as designed, the liquid is transferred at a low flow rate. Additional pressure equalization tubes would decrease available screen area. Also, the double-ended threaded cap is expensive to manufacture and to assemble with the coaxial tube.

SUMMARY OF INVENTION

It is therefore an object of this invention to provide an improved filter device for use in closed-system transfer and filtering of liquids.

It is a further object of this invention to provide such a filter device which resists clogging.

It is a further object of this invention to provide such a filter device which utilizes multiple gas return passages that are integral with the filter.

It is a further object of this invention to provide such a filter device that provides a large filter area.

It is a further object of this invention to provide such a filter device which provides a high rate of filtration.

It is a further object of this invention to provide such a filter device that enables accurate sampling of particles in a liquid.

A still further object of this invention is to provide such a filter device which is inexpensive to manufacture.

Yet another object of this invention is to provide such a filter device which is easy to use.

The invention results from the realization that a truly effective system for filtering liquid from a collection vessel into a receptacle vessel can be achieved by a device that forms an interference fit with the interior surfaces of the collection vessel and has a plurality of gas return passages disposed peripherally about a filter to rapidly and continuously equalize pressure between the vessels.

This invention features a device for filtering liquid from a collection vessel into a receptacle vessel. There are a conduit, a filter in the conduit, and a rim spaced from the filter and forming an interference fit with the interior surface of the collection vessel. The rim has a plurality of openings spaced about its periphery and the device further includes means for removably securing the conduit to the receptacle vessel and a plurality of gas return passages, arranged about the exterior of the conduit, which connect the receptacle to the openings in the rim.

In one embodiment the passages include a plurality of channels in the exterior surfaces of the conduit proximate a region of engagement between the conduit and the means for securing. In another embodiment, the passages include a plurality of vents in the means for securing, such as a plurality of recesses in the means for securing proximate the region of engagement between the means for securing and the conduit. The passages may also include a plurality of apertures established between the means for securing and the conduit.

The conduit may be tapered from the rim toward the filter so as to be conical between the rim and the filter. The means for securing may include means for threadably engaging the receptacle vessel. The filter device may further include means for guiding the open end of the collection vessel proximate the juncture of the conduit and the means for securing. The means for guiding may include collar means for forming an interference fit with at least the opening of the collection vessel; the collar means may be integrally connected to the means for securing.

In another embodiment, the means for guiding includes a plurality of external ribs disposed on the conduit and oriented from the rim toward the filter. The ribs may be axially oriented. The conduit may include means for forming a snap fit with the means for securing such as a projection on the conduit which is received by the means for securing. The projection may be an annular ridge and the conduit may further include stop means, spaced above the projection, for limiting axial engagement of the conduit with the means for securing. The filter may be a screen of predetermined mesh size and each opening in the rim may be no greater in size than the mesh size of the screen.

This invention also features an apparatus for filtering liquid, including a collection vessel having an open end, a receptacle vessel for receiving liquid from the collection vessel, a conduit, a filter in the conduit, and a rim spaced from the filter and forming an interference fit with the interior surfaces of the collection vessel. The rim includes a plurality of openings spaced about its periphery. The apparatus further includes means for removably securing the conduit to the receptacle vessel, and a plurality of gas return passages, arranged about the exterior of the conduit, which connect the receptacle to the openings in the rim. In one embodiment the receptacle vessel is a centrifuge tube.

DISCLOSURE OF PREFERRED EMBODIMENT

Figure 2:
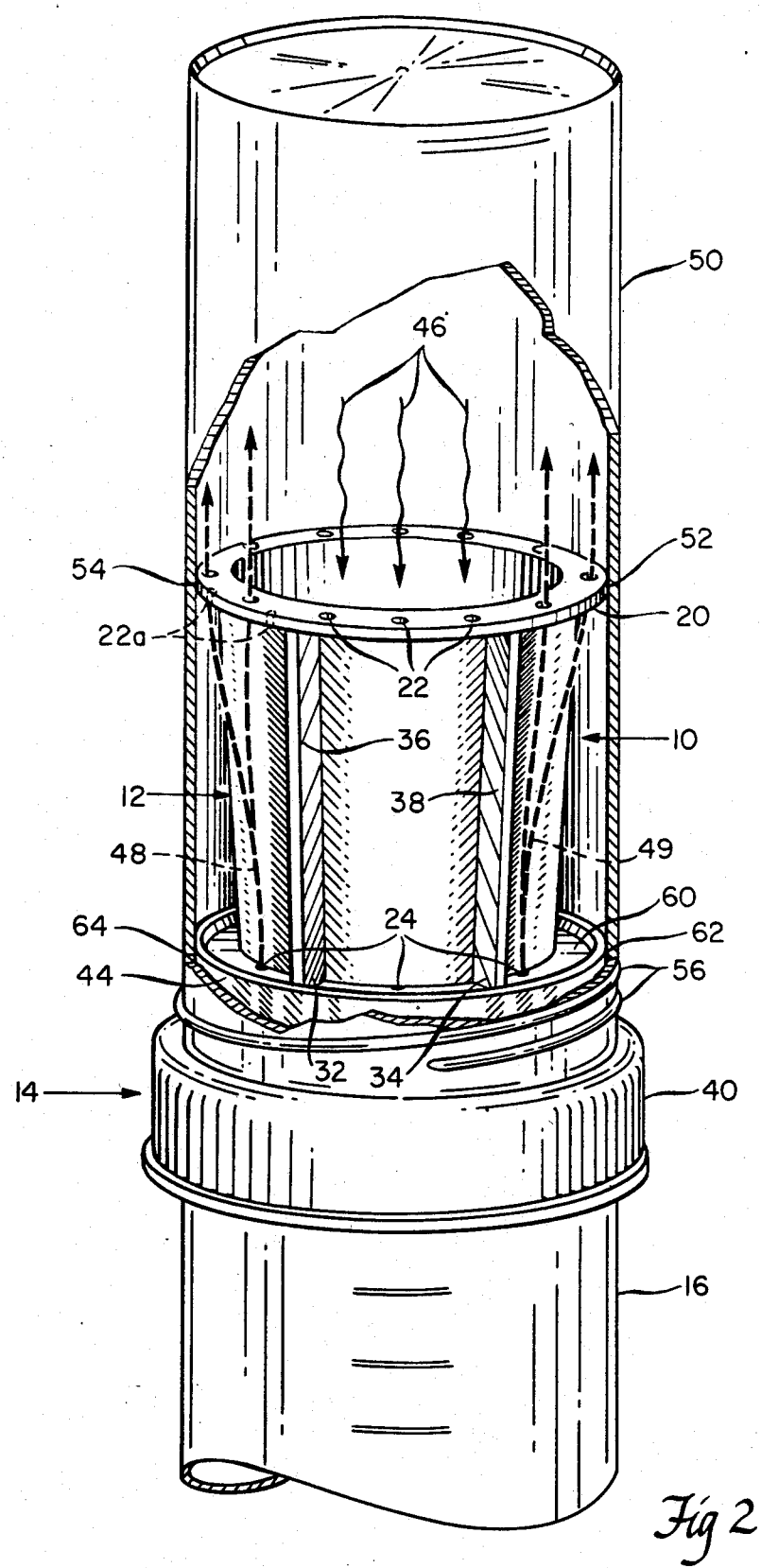

Other objects, features and advantages will occur from the following description of a preferred embodiment and the accompanying drawings, in which:

FIG. 1 is an exploded axonometric view of a filter device according to this invention and a centrifuge tube; and FIG. 2 is an axonometric partial cross-sectional view of an assembled filter apparatus according to this invention.

This invention may be accomplished by structure which forms an interference fit with the interior of a collection vessel, attaches to a receptacle vessel, and defines a plurality of gas return passages which enable gas to pass from the receptacle vessel to the collection vessel to equalize pressure between the vessels. The structure includes a conduit, a filter in the conduit and a rim spaced above the filter. The rim forms the interference fit with the collection vessel and includes a plurality of openings spaced about its periphery. The structure further includes an element for removably securing the conduit to the receptacle vessel. The gas return passages communicate with the openings in the rim and may include a combination of vents in the element for securing, recesses in the conduit, and apertures defined by both the element for securing and the conduit.

A filter device according to this invention can be constructed, depending on the mesh size selected for the device, to capture target particles on the filter or to pass liquid and small particles while blocking larger, undesired particles. Filter device 10, FIG. 1, performs the latter function and is directed to analysis of fecal material in an operation known as fecal compaction. Filter device 10 includes conduit 12 and element 14 and is shown with centrifuge tube 16 which serves as a receptacle for liquid filtered through filter 18 of conduit 12. Filter 18 is shown in a partial exposed view disposed at one end of conduit 12; alternatively, the filter is positioned at a distance from the end such as indicated in phantom by filter 18a. Rim 20 is spaced from filter 18 and similarly need not be positioned at an end of conduit 12.

Rim 20 includes openings 22, shown more clearly in FIG. 2, which communicate with vents 24 in element 14. In this construction, vents 24 are recesses in lip 26 of element 14; in another construction recesses 24a, shown in phantom in FIG. 1, are present on the exterior surface of conduit 12. Recesses 24a are open grooves that are cut or molded into conduit 12 and pass through ridge 30.

During assembly of filter device 10, conduit 12 is secured to element 14 by pressing ridge 30 past lip 26 to form a snap fit. Ends 32, 34 of ribs 36, 38 serve as stops which limit further axial engagement between conduit 12 and element 14. The limiting action of ends 32, 34 of ribs 36, 38 is seen more clearly in FIG. 2. Ends 32, 34 rest against shelf 60 in collar 44. Further axial engagement is also limited by the conical shape of conduit 12.

In operation, a fecal sample is placed into an uninverted collection vessel such as specimen vial 50, shown in an inverted position in FIG. 2, and is diluted with liquid. Threads 56 seal with a cap, not shown, to prevent contamination of specimen vial 50 before use and to seal the fecal sample within specimen vial 50 until the sample is filtered.

Filter device 10 and centrifuge tube 16 are assembled with each other: cap 40 of element 14 threadably engages threads 42 on centrifuge tube 16. Initially, conduit 12, element 14 and centrifuge 16 are oriented inversely to FIGS. 1 and 2 and rim 20 and then collar 44 are slid through the opening of the collection vessel. Ribs 36, 38 and the remaining ribs not visible in this view help guide filter device 10 into the collection vessel as well as add structural support to conduit 12.

In this construction, collar 44 also helps guide and, in addition, forms an interference fit with the opening of the collection vessel. Filter device 10, centrifuge tube 16 and specimen vial 50, FIG. 2, comprise filter apparatus 45. Once assembled, filter apparatus 45 is inverted to the orientation shown in FIG. 2. Liquid and particulates, including target parasite larvae and eggs, enter conduit 12 as indicated by arrows 46 while gas, typically air, from centrifuge tube 16 emerges through vents 24 and as indicated in phantom by dashed lines 48, 49 pass through openings 22 in rim 20 to equalize pressure between centrifuge tube 16 and specimen vial 50.

The interference fit between rim 20 and collection vessel 50 is depicted at regions 52, 54. The interference fit need not be continuous about the border of rim 20: channels 22a, shown in phantom, may be substituted for or used in conjunction with openings 22.

While during normal operation liquid does not enter openings 22, entrapment of particles above a predetermined size is ensured by establishing the size of openings 22 to be no greater than the mesh size of the filter. Acceptable mesh sizes of filter 18 and the size of openings 22 range from 18 to 25 mm for fecal compaction operations.

The interference fit between collar 44 and specimen vial 50, shown at areas 62, 64, ensures that if liquid inadvertently passes through rim 20, the liquid is arrested at shelf 60 by interference fit 62, 64 instead of exiting between specimen vial 50 and cap 40. If vents 24 are sufficiently large to overcome surface tension, the trapped liquid then drains through vents 24.

In this construction gas return passages are defined by openings 22 in rim 20 and vents 24 in shelf 60; additional structure defining air passages is not present and therefore gas travel as depicted by lines 48, 49 is unguided. In other constructions, ribs 36, 38, are extended to contact the interior of specimen vial 50 and define independent passages between them or are enlarged and provided with internal passages communicating through shelf 60 with centrifuge tube 16 and through rim 20 with the upper portion of specimen vial 50. For ease of manufacture, however, it is desirable to manufacture conduit 12 separate from element 14, as shown in FIG. 1, and to omit structure between openings 22 and vents 24. A plastic material such as high-density polyethylene is acceptable for fabricating the components of filter device 10.

In any construction, a filter device according to this invention includes one or more gas return passages independent of the filter itself. Such a device resists clogging and provides a high rate of filtration. Further, it is essentially nonreversable: little or no liquid returns from centrifuge tube 16 to specimen vial 50 if filter apparatus 45 is reinverted from the orientation shown in FIG. 2.

A filter device and apparatus according to this invention are easy to assemble before filtering, to use during filtering, and also to contain undesired, filtered debris. After use, filter device 10 can be decoupled from centrifuge tube 16 and simply discarded while still attached with specimen vial 50. Alternatively, device 10 can be pull-separated from specimen vial 50 and washed for reuse. If reuse is desired, filter device 10 preferably is fabricated from high-density polyethylene.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A device comprising: means for filtering liquid from a collection vessel into a otherwise closed receptacle vessel, including,
   a conduit;
   a filter in said conduit;
   a rim spaced from said filter and forming an interference fit with the interior surfaces of the collection vessel, said rim having a plurality of openings spaced about its periphery;
   means for removably, securing said conduit to the receptacle vessel; and
   a plurality of gas return passages, arranged about the exterior of said conduit, which connect the receptacle vessel to the openings in said rim to equalize pressure between the receptacle vessel and its exterior during filtration and enhance transfer of liquid while minimizing clogging of said openings.

2. The filter device of claim 1 in which said passages include a plurality of channels in the exterior surfaces of said conduit proximate a region of engagement between said conduit and said means for securing.

3. The filter device of claim 1 in which said passages include a plurality of vents in said means for securing.

4. The filter device of claim 3 in which said vents include a plurality of recesses in said means for securing proximate a region of engagement between said means for securing and said conduit.

5. The filter device of claim 1 in which said passages include a plurality of apertures established between said means for securing and said conduit.

6. The filter device of claim 1 in which said conduit is tapered from said rim toward said filter.

7. The filter device of claim 6 in which said conduit is a conical section between said rim and said filter.

8. The filter device of claim 1 in which said means for securing includes means for threadably engaging the receptacle vessel.

9. The filter device of claim 1 further including means for guiding the open end of the collection vessel proximate the juncture of said conduit and said means for securing.

10. The filter device of claim 9 in which said means for guiding includes collar means for forming an interference fit with at least the opening of the collection vessel.

11. The filter device of claim 10 in which said collar means is integrally connected to said means for securing.

12. The filter device of claim 9 in which said means for guiding includes a plurality of external ribs disposed on said conduit and oriented from said rim toward said filter.

13. The filter device of claim 12 in which said ribs are axially oriented.

14. The filter device of claim 1 in which said conduit includes means for forming a snap fit with said means for securing.

15. The filter device of claim 14 in which said means for forming a snap fit includes a projection which is received by said means for securing.

16. The filter device of claim 15 in which said projection is an annular ridge.

17. The filter device of claim 15 in which said conduit further includes stop means, spaced above said projection, for limiting axial engagement of said conduit with said means for securing.

18. The filter device of claim 1 in which said filter is a screen of predetermined mesh size.

19. The filter device of claim 18 in which each opening in said rim is no greater in size than the mesh size of said screen.

20. A device comprising: means for filtering liquid during closed system transfer of the liquid from a collection vessel into a receptacle vessel, including,
   a conduit;
   a filter in said conduit;
   a rim spaced from said filter and forming an interference fit with the interior surfaces of the collection vessel, said rim having a plurality of openings spaced about its periphery;
   means for removably securing said conduit to the receptacle vessel;
   means for guiding the open end of the collection vessel proximate the juncture of said conduit and said means for securing; and
   a plurality of gas return passages, arranged about the exterior of said conduit, which connect the receptacle vessel to the openings in said rim to equalize pressure between the vessels during filtration and enhance transfer of the liquid while minimizing clogging of said openings.

21. The apparatus of claim 1 in which said receptacle vessel is a centrifuge tube.

22. An apparatus for filtering liquid during closed system transfer of the liquid, comprising:
   a collection vessel having an open end;
   a receptacle vessel for receiving liquid from said collection vessel;
   a conduit;
   a filter in said conduit;
   a rim associated with said conduit, spaced from said filter, and forming an interference fit with the interior surfaces of said collection vessel, said rim having a plurality of openings spaced about its periphery;
   means for removably securing said conduit to said receptacle vessel;
   a plurality of gas return passages, arranged about the exterior of said conduit, which connect said receptacle vessel to the openings in said rim; and
   said collection vessel and said receptacle vessel establishing a closed system between them, and said gas return passages equalizing pressure between said vessels during filtration and enhancing transfer of the liquid while minimizing clogging of said openings.

* * * * *